(12) United States Patent
Li et al.

(10) Patent No.: US 9,649,276 B2
(45) Date of Patent: May 16, 2017

(54) MINERAL SUPPLEMENTATION OF BEVERAGES

(71) Applicant: DSM IP ASSETS B.V., Heerlen (NL)

(72) Inventors: Feng Li, Echt (NL); Leonardus Gerardus Bernardus Bremer, Echt (NL); Remco Tuinier, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 104 days.

(21) Appl. No.: 14/404,809

(22) PCT Filed: May 27, 2013

(86) PCT No.: PCT/IB2013/054365
§ 371 (c)(1),
(2) Date: Dec. 1, 2014

(87) PCT Pub. No.: WO2013/179206
PCT Pub. Date: Dec. 5, 2013

(65) Prior Publication Data
US 2015/0150800 A1    Jun. 4, 2015

(30) Foreign Application Priority Data

Jun. 1, 2012 (EP) .................................. 12170516

(51) Int. Cl.
| | | |
|---|---|---|
| *A61K 9/107* | (2006.01) | |
| *A23L 2/52* | (2006.01) | |
| *A23L 2/02* | (2006.01) | |
| *A23C 9/152* | (2006.01) | |
| *A61K 33/26* | (2006.01) | |
| *A23P 10/30* | (2016.01) | |
| *A23L 33/165* | (2016.01) | |

(52) U.S. Cl.
CPC .......... *A61K 9/1075* (2013.01); *A23C 9/1522* (2013.01); *A23L 2/02* (2013.01); *A23L 2/52* (2013.01); *A23L 33/165* (2016.08); *A23P 10/30* (2016.08); *A61K 33/26* (2013.01); *A23V 2002/00* (2013.01)

(58) Field of Classification Search
None
See application file for complete search history.

(56) References Cited

U.S. PATENT DOCUMENTS

| | | |
|---|---|---|
| 6,994,876 B1 | 2/2006 | Sher et al. |
| 2006/0240151 A1 | 10/2006 | Walker et al. |
| 2009/0124572 A1 | 5/2009 | Nelson |

FOREIGN PATENT DOCUMENTS

| | | |
|---|---|---|
| EP | 2 174 657 | 4/2010 |
| WO | WO 98/48648 | 11/1998 |
| WO | WO 00/51446 | 9/2000 |
| WO | WO 2008/028264 | 3/2008 |

OTHER PUBLICATIONS

International Search Report for PCT/IB2013/054365 mailed Oct. 9, 2013.
Mehansho Haile: "Iron Fortifiation Technology Development: New Approaches", The Journal of Nutrition, vol. 136, No. 4, Apr. 1, 2006, pp. 1059-1063.

*Primary Examiner* — David J Blanchard
*Assistant Examiner* — Sarah Chickos
(74) *Attorney, Agent, or Firm* — Nixon & Vanderhye P.C.

(57) ABSTRACT

The present invention is directed to metal supplementation of beverages. More particularly, it is directed to a metal containing complex coacervate core micelle comprising a negatively charged chelating agent, a low molecular weight natural food-grade polymeric cation, and water. It is also directed to a process to produce said metal containing complex coacervate core micelle, and to the use of said metal containing complex coacervate core micelle to supplement beverages with a source of highly bioavailable metal. It is also related to a beverage comprising said metal containing complex coacervate core micelle.

4 Claims, 5 Drawing Sheets

MINERAL SUPPLEMENTATION OF BEVERAGES

This application is the U.S. national phase of International Application No. PCT/IB2013/054365 filed 27 May 2013 which designated the U.S. and claims priority to EP 12170516.4 filed 1 Jun. 2012, the entire contents of each of which are hereby incorporated by reference.

The present invention relates to the field of metal supplementation of beverages. More particularly, it is directed to a metal containing complex coacervate core micelle comprising a negatively charged chelating agent, a low molecular weight natural food-grade polymeric cation, and water. It is also directed to a process to produce said metal containing complex coacervate core micelle, and to the use of said metal containing complex coacervate core micelle to supplement beverages with a source of highly bioavailable metal. It is also related to a beverage comprising said metal containing complex coacervate core micelle.

Among metal deficiencies, iron deficiency anemia is a serious nutrition related health problem, affecting more than 3 billion people in the world. While iron deficiency is one of the direct causes of anemia, it is also the cause of various other physiological disorders like energy deficiency, poor growth and development. Food fortification programmes are usually considered the most cost-effective and sustainable approach to combat iron (Fe) deficiency. However, the success of an iron fortification programme depends largely on the careful choice of the Fe compound, and of the food matrix.

There are well-recognized problems associated with adding mineral supplements to foods and beverages. For example, many such mineral supplements tend to be rather insoluble, and, therefore, not very useful in beverages, or tend to have a bad taste (metallic taste) or unacceptable mouth feel. Moreover, iron supplements tend to discolour foodstuffs, or to be organoleptically unsuitable. It is also particularly difficult to formulate beverages containing iron supplements in as much as iron compounds tend to form insoluble iron hydroxide polymers in solution and interact with other minerals and other materials. This interaction not only affects the organoleptic and aesthetic properties of the beverages, but also undesirably affects the nutritional bioavailability of the iron supplements.

WO 2011/159665 discloses encapsulated nutrient salts comprising nutrient salt particles encapsulated with a water-insoluble chitosan-stearic acid complex. However, this encapsulation is based on microemulsion requiring an oil phase and is not stable over long term storage in a beverage.

WO 2009/029407 discloses the delivery and controlled release of encapsulated water-insoluble flavorants. It is based on complex coacervate comprising whey protein and polysaccharide to form a complex based on electrostatic attraction. However, the particle size are all above 500 nm, which when used in solution result in turbidity.

WO 2010116379 discloses an iron fortified tea in a dried form comprising 99.5 to 99.88% of tea, 0.1 to 0.3% of iron salt, and 0.02 to 0.2% of starch base. This fortified tea is produced by spraying the iron solution on dried tea. However, this technology does not allow producing liquid beverages fortified with iron because of precipitation of the iron salt.

The inventors of the present application now surprisingly found a new composition useful for metal fortification of beverages. This composition is cost effective, uses a homopolymer mixture, is prepared from products that are all considered food grade on a global basis, are stable with time as such and when mixed with beverages, it does not degrade during pasteurization, it does not react with polyphenols, it provides excellent metal bioavailability it does not color the supplemented beverage, and does not produce a metallic taste. Moreover, this composition based on aqueous soluble components self assembles into particles. In addition, these food-grade complex coacervate particles allow to use very high concentration of metal (e.g.: iron) in aqueous solution while keeping the solution stable and transparent.

Therefore, the present invention provides a metal containing complex coacervate core micelle comprising 80 to 99 wt.-% of a negatively charged chelating agent, 0.2 to 10 wt.-% of a low molecular weight natural food-grade polymeric cation, 0.5 to 10 wt.-% of a metal cation and water, wherein wt.-% means dry weight percent based on the total weight of the complex coacervate core micelle, and wherein the average particle size as measured by dynamic light scattering is between 10 and 150 nm.

Unless otherwise specified, all percentages in the present application are expressed as percent of dry weight based on the total weight of the complex coacervate core micelle.

A complex coacervate is a tiny spherical droplet of assorted organic molecules which is held together by hydrophobic forces from a surrounding liquid. Coacervation is a process of spontaneous phase separation that occurs when two oppositely charged polyelectrolytes are mixed in an aqueous solution. The electrostatic interaction between the two species of micromolecules results in the separation of a coacervate (polymer-rich phase) from the supernatant (polymer-poor phase). This phenomenon can be used to form nanospheres and encapsulate a variety of compounds. The encapsulation process can be performed entirely in aqueous solution and at low temperatures without providing any energy.

By definition, nanospheres or ultrafine particles are sized between 1 and 150 nanometers. The advantage of nanospheres is that clear suspensions are possible since the interaction of the particle surface with the solvent is strong enough to overcome density differences, which otherwise usually result in a material either sinking or floating in a liquid.

A micelle is an aggregate of surfactant molecules dispersed in a liquid colloid. A typical micelle in aqueous solution forms an aggregate with the hydrophilic "head" regions in contact with surrounding solvent, sequestering the hydrophobic single tail regions in the micelle centre. Complex coacervate core micelles have the property to self assemble when the raw materials (polymeric cation and chelating agent) are mixed in a defined way and in a defined ratio.

For the present invention the metal cation can be selected from iron, calcium, and zinc, but is preferably $Fe^{2+}$.

Chelation is the formation or presence of two or more separate coordinate bonds between a polydentate (multiple bonded) ligand and a single central atom. Usually these ligands are organic compounds, and are called chelants, chelators, chelating agents, or sequestering agents. For the present invention, any negatively charged chelating agent selected form common organic compounds can be used. More preferably, the chelating agent has a ring-like structure (having the shape of ring) and even more preferably, it is sodium hexametaphosphate.

Sodium hexametaphosphate (SHMP) is a hexamer of composition $(NaPO_3)_6$. Sodium hexametaphosphate of commerce is typically a mixture of polymeric metaphosphates, of which the hexamer is one, and is usually the compound referred to by this name. It is more correctly termed sodium polymetaphosphate. It is prepared by melting monosodium orthophosphate, followed by rapid cooling.

The low molecular weight natural food-grade polymeric cation is defined as any polymeric material that is deemed by the US Food and Drug Administration to be safe for use in food and beverage products. Suitable natural food-grade polymeric cation for the present invention include but are not limited to dairy proteins including whey proteins, and caseins, gelatin, egg albumin, vegetable proteins, microbial proteins, legume proteins, and chitosan. Preferred low molecular weight natural food-grade polymeric cation according to the present invention is chitosan with a polymerization degree between 5 and 100, more preferred, with a polymerization degree between 10 and 50, even more preferred, with a polymerization degree between 10 and 20. Chitosan is a linear polysaccharide composed of randomly distributed β-(1-4)-linked D-glucosamine (deacetylated unit) and N-acetyl-D-glucosamine (acetylated unit). Chitosan is produced commercially by deacetylation of chitin, which is the structural element in the exoskeleton of crustaceans.

The metal encapsulated within such complex coacervate core micelle is stabilized due to the protection of the polymeric corona, and antioxidant efficiency is increased due to the presence of the chelating agent.

Because SHMP is partially interacting with chitosan, the metal chelating efficiency is reduced. The interaction of SHMP and chitosan is determined by the concentration of these two molecules and environmental conditions, like, pH and temperature. This means the interaction or chelation potential of SHMP and iron can be adjusted by the person skilled in the art by influencing the interaction of SHMP and chitosan. As a result, the bioavailability of the iron can be controlled. Furthermore, these self assembled micelle particles are hollow objects, and they can encapsulate other food ingredients, for instance, flavor molecules, vitamins.

In another embodiment, the present invention relates to metal containing complex coacervate core micelle according to the invention as described above and further comprising a water soluble food flavouring agent and/or vitamin in the aqueous phase, or a fat soluble food flavouring agent and/or vitamin in the shell of the micelle. Preferably, it comprises between 0 and 10 wt.-% of a water or fat soluble flavouring agent and/or vitamin based on the total weight of the complex coacervate core micelle.

Although the terms "flavoring" or "flavorant" in common language denote the combined chemical sensations of taste and smell, the same terms are usually used in the fragrance and flavors industry to refer to edible chemicals and extracts that alter the flavor of food and food products through the sense of smell. Due to the high cost or unavailability of natural flavor extracts, most commercial flavorants are nature-identical, which means that they are the chemical equivalent of natural flavors but chemically synthesized rather than being extracted from the source materials. Any common food-grade flavoring agent can be used in the composition according to the present invention. Preferred flavorants are selected from almond nut, amaretto, anisette, brandy, cappuccino, mint, cinnamon, cinnamon almond, creme de menthe, Grand Mariner, peppermint stick, pistachio, sambuca, apple, chamomile, cinnamon spice, creme, creme de menthe, vanilla, French vanilla, Irish creme, Kahlua, mint, peppermint, lemon, macadamia nut, orange, orange leaf, peach, strawberry, grape, raspberry, cherry, coffee, chocolate, cocoa, mocha and the like, and any mixtures thereof; as well as flavorant/aroma enhancers such as acetaldehyde diacetyl, isoamylacetate, benzaldehyde, cinnamic aldehyde, ethyl propionate, methyl anthranylate, limonene, ethyl-2,4-decadienoate, allylhexanoate, ethyl maltol, ethylvanillin, methyl salicylate or mixtures thereof, herbs, spices, as well as any mixtures thereof.

Water soluble vitamins according to the present invention can be selected from vitamin B1 (thiamine), vitamin B2 (riboflavin), vitamin B6 (pyridoxine), niacin (nicotinic acid), vitamin B12, folic acid, pantothenic acid, biotin, and vitamin C.

Fat soluble vitamins according to the present invention are selected from vitamins A, D, E, and K.

In a preferred embodiment, the present invention relates to a metal containing complex coacervate core micelle comprising
- 85 to 99 wt.-% sodium hexametaphosphate,
- 0.4 to 8 wt-% chitosan with a polymerisation degree between 10 and 20,
- 0.6 to 6 wt.-% $Fe^{2+}$,
- 0 to 10 wt. % of a water or fat soluble flavouring agent and/or vitamin,
- and water, wherein wt.-% means dry weight percent based on the total weight of the complex coacervate core micelle, and wherein the average particle size as measured by dynamic light scattering is between 10 and 150 nm.

In a more preferred embodiment, the present invention relates to a metal containing complex coacervate core micelle comprising
- 85 to 99 wt.-% sodium hexametaphosphate,
- 0.4 to 8 wt-% chitosan with a polymerisation degree between 10 and 20,
- 0.6 to 6 wt.-% $Fe^{2+}$,
- 0 to 10 wt. % of a water or fat soluble flavouring agent and/or vitamin,
- and water, wherein the sodium hexametaphosphate is at a concentration comprised between 5 and 350 mg/ml, wherein wt.-% means dry weight percent based on the total weight of the complex coacervate core micelle, and wherein the average particle size as measured by dynamic light scattering is between 10 and 150 nm.

The metal containing complex coacervate core micelle according to the present invention have an average particle size of between 10 and 150 nm, more preferably, an average particle size of between 50 and 100 nm. The particle size can be adjusted by the molecular weight of the natural food grade polymerization. e.g.: Particle size comprised between 10 and 150 nm will be obtained when using chitosan with a degree of polymerization of less than 15. Particle size is measured by dynamic light scattering on an ALV light-scattering apparatus.

In another embodiment, the present invention also provides a process for the manufacture of a metal containing complex coacervate core micelle as described above comprising the steps of:
i) preparing an aqueous solution of a negatively charged chelating agent A),
ii) preparing an aqueous solution of a metal salt B),
iii) mixing 100 parts of A) with 20 parts of B) at equimolar concentration, and incubating the resulting mixture at room temperature, to produce the resulting chelated metal solution C),
iv) preparing an aqueous solution of a low molecular weight natural food-grade polymeric cation in a citric acid buffer solution at pH between 4 and 6, D),
v) adding drop-wise the chelated metal solution D) to 880 parts of the solution C) while stirring.

Preferably, the present invention provides a process for the manufacture of a metal containing complex coacervate core micelle as described above comprising the steps of:
i) preparing an aqueous solution of a negatively charged chelating agent A) at 1 to 500 mM,
ii) preparing an aqueous solution of a metal salt B) at 1 to 500 mM,
iii) mixing 100 parts of A) with 20 parts of B) at equimolar concentration, and incubating the resulting mixture for 5 minutes to 5 days at room temperature, to produce the resulting chelated metal solution C),
iv) preparing an aqueous solution of a low molecular weight natural food-grade polymeric cation at a concentration of 0.1 to 1 mg/ml in a citric acid buffer solution at pH between 4 and 6, D),
v) adding drop-wise the chelated metal solution D) to 880 parts of the solution C) while stirring.

More preferably, the incubation time of step iii) is at least 20 minutes, preferably at least 50 minutes, more preferably, at least 90 minutes, and not more than 5 days, preferably not more than 24 hours, more preferably, not more than 8 hours, even more preferably, not more than 5 hours.

Even more preferably, for the process according to the present invention, the negatively charged chelating agent is sodium hexametaphosphate, the metal salt is $FeSO_4$, and the low molecular weight natural food-grade polymeric cation is chitosan with a polymerisation degree between 10 and 20. More preferably, the sodium hexametaphosphate and FeSO4 solutions of steps i) and ii) are each at a concentration of between 50 and 150 mM, and chitosan of step iv) is at a concentration of between 0.4 to 0.8 mg/ml. Even more preferably, the sodium hexametaphosphate and FeSO4 solutions are each at a concentration of 100 mM, and chitosan is at a concentration of 0.6 mg/ml.

It is critical in step v) of the present process to add drop-wise solution D) to solution C). The surface charge and stabilization mechanism will be completely different if it is done the other way around, and it would result in micrometer sized precipitates instead of well soluble and stable nanoparticles as in the present invention.

In another embodiment, the present invention provides the use of metal containing complex coacervate core micelle according to the present invention, for supplementing a beverage with 1 to 60 mg metal/liter. For the present invention, beverage, is a liquid which is specifically prepared for human consumption. For the purpose of the present invention, beverage are ready-to-drink beverages, beverage concentrates, syrups, shelf-stable beverages, refrigerated beverages, frozen beverages, and the like, and it also includes water and flavored water. In a preferred embodiment, beverages are selected from juice, non carbonated soft drinks, milk and fruit juice. Beverage products may be pasteurized using common technologies like ultra high temperature treatment (UHT) and/or high temperature-short time treatment (HTST).

The present invention is also directed to a beverage comprising a metal containing complex coacervate core micelle according to any of the present invention.

The invention is further illustrated by the following examples.

EXAMPLES

Example 1

Preparation of Iron Containing Complex Coacervate Core Micelle

Sample Preparation:

Iron (II) sulphate and low molecular weight chitosan (degree of polymerization, n<15) was purchased from Sigma-Aldrich. Sodium hexametaphosphate (SHMP) was purchased from J.T. Baker. Three stock solutions were prepared in aqueous solution at following concentrations: (A) 100 mM SHMP, (B) 100 mM $FeSO_4$ and (C) 20 mg/ml chitosan with pH<3. 0.5 M acetic acid buffer at pH 5 was further diluted and used as the buffer solution to prepare sample. As a start, 100 μl A was added to 20 μl B, and the reaction time between A and B correlates to the binding efficiency of iron and chelating agent SHMP. This reaction time can be varied from minutes to days. In the present examples, incubation time was for 1 hour. The longer the reaction time, the stronger the iron will bind to SHMP. In the mean time, 25 μl C was diluted with 755 μl miliQ water in the presence of 100 μl acetic acid buffer. Once both mixtures are ready, iron and SHMP solution was added drop wise to the diluted chitosan solution with stirring. The weight percentage of the final mixture is the following: 6 mg/ml SHMP, 0.4 mg/ml $Fe^{2+}$, 0.5 mg/ml chitosan. These weight percentages can be increased to: 325 mg/ml SHMP, 2.6 mg/ml $Fe^{2+}$, and 1.3 mg/ml chitosan to make stable self assembled particles.

Characterization of the Complex Coacervate Core Micelle:

Dynamic light scattering (DLS) was carried out on an ALV light-scattering apparatus (ALV, Langen, Germany). All experiments were performed at a scattering angle of 90°. Temperature was controlled by using a Haake C35 thermostat. The hydrodynamic radius was calculated from cumulant fits or a CONTIN multi-exponential fit. The relative intensity was obtained according to the intensity ratio of samples and the toluene. Static light scattering (SLS) measurement was done on same ALV apparatus, and the detector angle varies from 24° to 140°. Titration measurement and ζ-potential measurements were performed on Zetasizer (Malvern, UK). Scattering light intensity for the titration samples were also taken from the measurements on Zetasizer.

Transmission electron microscopy (TEM) measurements were performed on a JEOL 1200 EX electron microscope operating at 100 kV. Images were recorded with a 1k CCD camera. Sample was dried on copper grid overnight before measuring.

UV spectrum measurement was performed on UV-2450 (Shimadzu) with 0.05 M acetic acid as the reference. The concentration of tannic acid, the polyphenol used in this study is 0.15 mg/ml.

Figure 1:
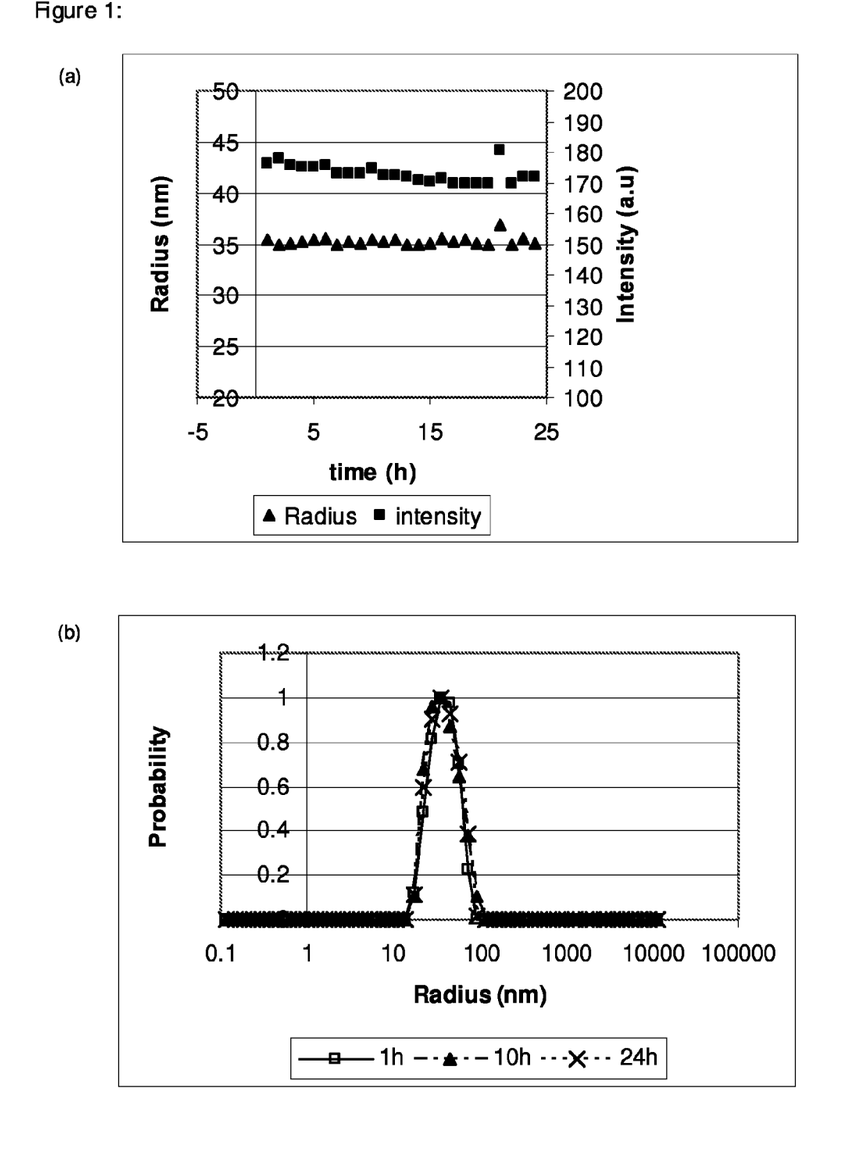
FIG. 1: DLS measurement of particle stability as a function of time (a) triangle belongs to the measured average particle radius according to cumulant fit and square belongs to the average scattered light intensity. (b) particle size distribution as a function of incubation time (1, 10 and 24 hours) according to contin analysis.

Samples prepared at relatively low concentration (6 mg/ml SHMP, 0.4 mg/ml $Fe^{2+}$, 0.5 mg/ml chitosan) were diluted ten times and measured with DLS at 20° C. for 24 hours. Both average particle size, about 70 nm, scattered light intensity, as shown in FIG. 1a, and particle size distribution, as shown in FIG. 1b, does not change significantly within the indicated measuring time. This indicates the particles remain very stable at constant temperature, 20° C.

Figure 2:
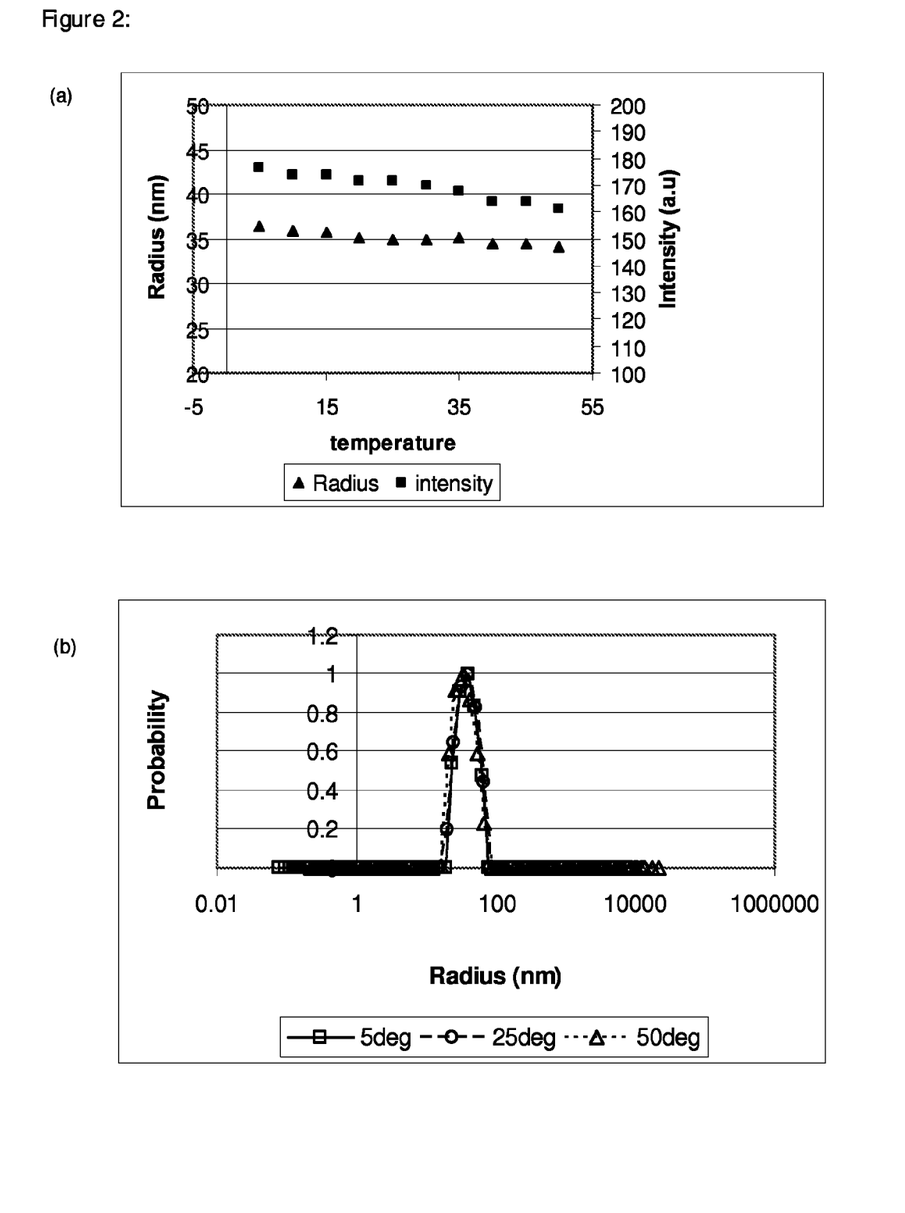
FIG. 2: DLS measurement of particle stability as a function of temperature (a) triangle belongs to the measured average particle radius according to cumulant fit and square belongs to the average scattered light intensity (b) particle size distribution as a function of incubation temperature (5, 25 and 50 degrees Celsius) according to contin analysis.

To check if the particle stability is sensitive to temperature, we performed DLS measurement at different temperatures. Same samples as used for the stability studies were prepared and measured every 5° C. with DLS between 5° C. and 50° C. Results are shown in FIG. 2. Average particle size, scattered light intensity, FIG. 2a, and particle size distribution, FIG. 2b, slightly decreased upon increasing temperature. The difference between 5° C. and 50° C. is rather small. This demonstrates that the particles size and shape remain relatively constant within the temperature range 5 to 50° C.

Figure 3:
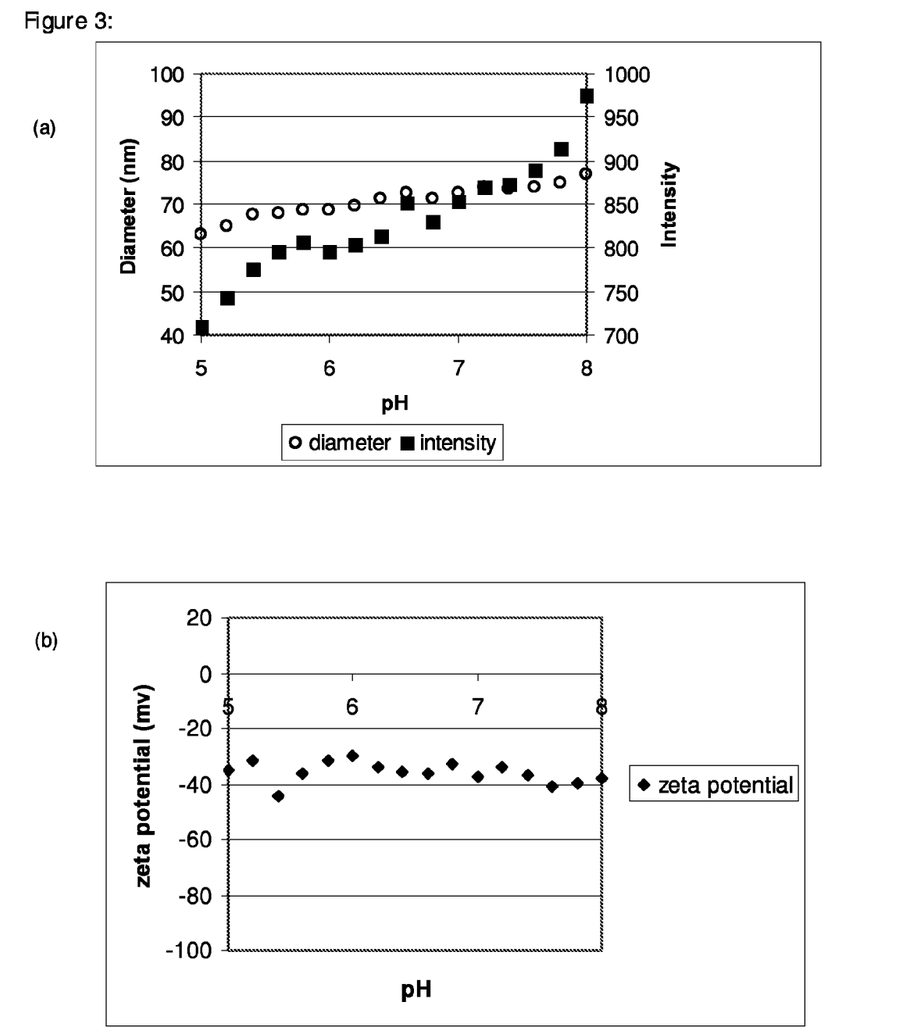
FIG. 3: Titration measurement of particle stability as a function of pH (a) circle belongs to the measured average particle radius according to cumulant fit and square belongs to the average scattered light intensity (b) ζ-potential as a function of pH.

These particles are stable over time and reasonably constant within the temperature of 5° C. to 50° C. To have better understanding of pH sensitivity of these particles and to have in depth knowledge about the composition of them, we performed pH titration measurements with Zeta sizer. Meanwhile we followed the ζ-potential change as a function of pH. Samples prepared at relatively low concentration (6 mg/ml SHMP, 0.4 mg/ml $Fe^{2+}$, 0.5 mg/ml chitosan) were diluted ten times and titrated with 0.1M NaOH. Results are shown in FIG. 3. Particle size as well as scattered light intensity increase upon increasing pH, FIG. 3a. However, the ζ-potential of the particle remains roughly constant, −40 mV, within the pH range of 3-8.

The negative ζ-potential of the particles indicates SHMP is the stabilizing functional group on the outside of the particle and SHMP groups are (partially) located on the surface of the particle. To further verify this observation and identify if SHMP and chitosan can self assemble into stable particles without addition of iron, we prepared the following sample and performed the titration measurements afterwards. Samples containing 6 mg/ml SHMP and 0.5 mg/ml chitosan were prepared first, $Fe^{2+}$ was added drop wise to reach the concentration of 0.4 mg/ml at the end. This sample was diluted ten times and titration measurement on the diluted sampler was performed with the zeta-sizer. Comparing with the previous titration measurement, both particle sizes as well the scattered light intensity increase significantly: Dh at pH 5 increases from 63 nm to 90 nm, meanwhile the scattered light intensity almost tripled, from 700 kHz to 2000 kHz (compare FIG. 3a and FIG. 4a). This change indicates the order of addition of iron to the mixture strongly influences the morphology and/or composition of the self assembled particles. Moreover, ζ-potential of the sample gradually decreases from −20 mV at the beginning of titration to −40 mV, as shown in FIG. 4b. The initial fluctuation of the ζ-potential can be overcome if the sample is equilibrated more than one hour before doing titration measurements, the measured ζ-potential will then keep roughly constant at −40 mV. This can be explained by the fact that time is needed to allow for reorganization of the complex to reach equilibrium upon addition of iron.

Figure 4:
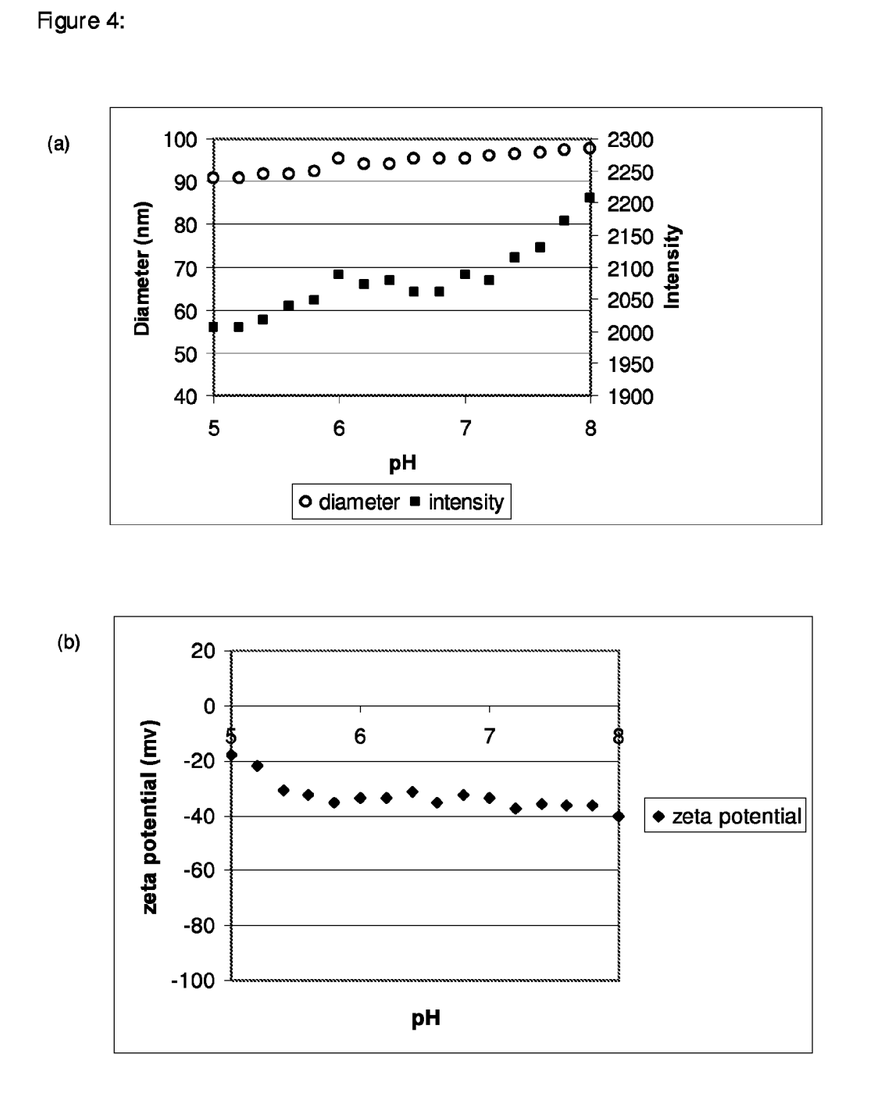
FIG. 4: Titration measurement of particle stability as a function of pH (a) circle belongs to the measured average particle radius according to cumulant fit and square belongs to the average scattered light intensity (b) ζ-potential as a function of pH.

These results indicate upon addition of iron to the mixture of SHMP and chitosan, a second layer of SHMP and chitosan complex most likely will associate to the particle. This explains the particle size increase as well as scatted light increasing upon iron addition. It seems iron is used as a cationic bridge here to bind the "core" of the particle with the extra layer of the SHMP and chitosan complex.

Besides stability and pH sensitivity of the particles, the iron encapsulated in this manner will give much less discoloration issue, and the binding strength of iron and chelating agent, SHMP, can be controlled kinetically. In practice this means that increasing the incubation time of SHMP with iron before addition of chitosan will strengthen the binding efficiency.

Figure 5:
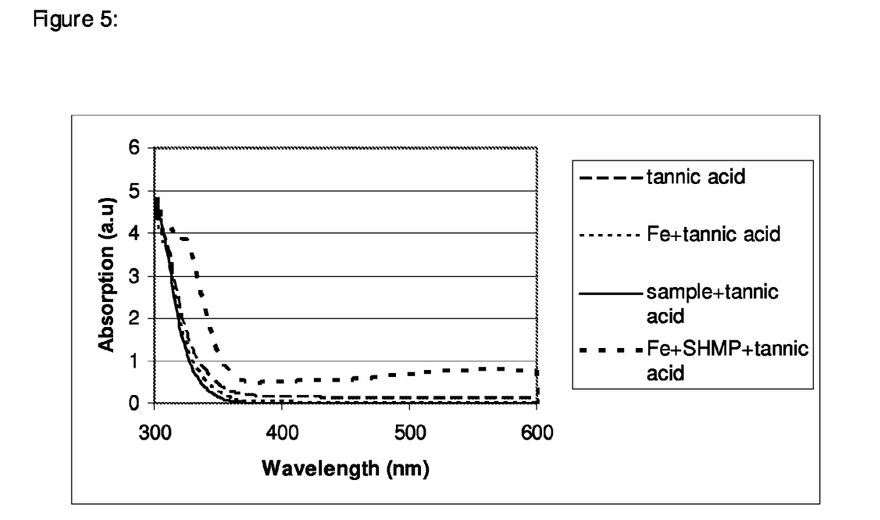
FIG. 5: UV spectra of polyphenol and iron containing mixtures.

Discoloring is usually related to reaction of iron with polyphenol. It is commonly assumed that iron forms a complex with polyphenol and the complex appear as dark blue giving problems in most food applications (Perron et al. 2010, Dalton Trans 39, 9982). Once iron binds strongly to SHMP, the probability of forming a complex with polyphenol is small. Hence discoloration is severely suppressed. We use UV spectrophotometry to probe the formation of iron polyphenol complex and compare the UV absorption spectrum with reference samples, results are shown in FIG. 5. Iron and polyphenol, tannic acid, forms complex quickly, and the characteristic UV absorption peak of the iron polyphenol complex appears around 550 nm. It has to be noted that the steady state of maximum UV absorption can only be reached more than ten hours after the sample was prepared under current experimental conditions. We noticed kinetic effect apparently associates with the formation of iron polyphenol complex. Contrary to the iron and tannic acid mixture, when iron first binds to SHMP and then combines with tannic acid, there is hardly any iron polyphenol complex being formed, which is indicated by the fact that no detectable UV absorption appears at 550 nm (FIG. 5). The sample mixture containing 0.6 mg/ml SHMP, 0.04 mg/ml $Fe^{2+}$, and 0.05 mg/ml chitosan with tannic acid gives slightly more UV absorption comparing with the reference sample composed of only iron, SHMP and tannic acid.

This difference explains the binding strength of iron and SHMP is influenced by the presence of chitosan. The binding strength relates to the bioavailability of the iron, which can now be controlled by the moment of introducing chitosan to SHMP and iron mixture.

Figure 6:
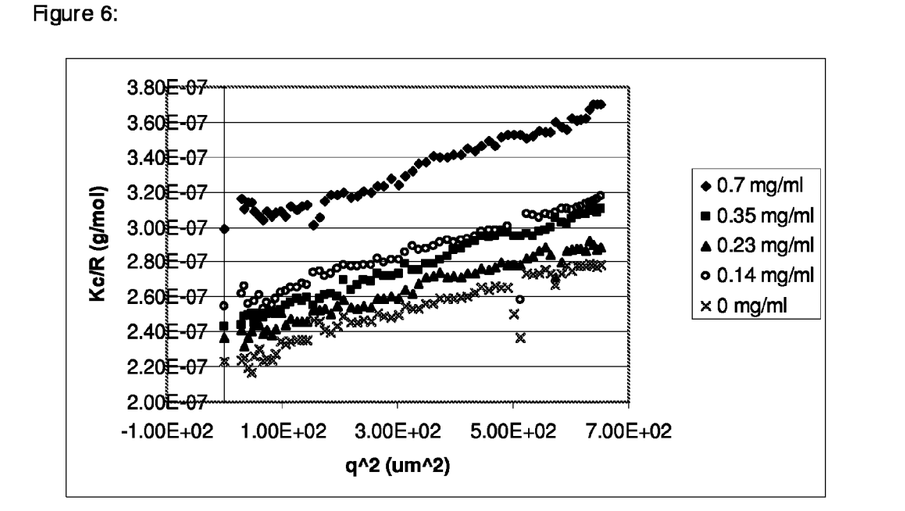
FIG. 6: SLS Zimm-plot of particle

To this end, we have shown the pH and temperature sensitivity of the particle. We also showed the potential of manipulating the iron bioavailability by carefully design the sample preparation procedure. From to the ζ-potential measurements it followed that SHMP is present on the surface of the particle. Further, there is no picture about the internal morphology of these particles. To further characterize these particles, we performed SLS studies on a sample containing 0.6 mg/ml SHMP, 0.04 mg/ml $Fe^{2+}$, and 0.05 mg/ml chitosan. The results of the measured scattered intensity for various scattering angles and particle concentrations are shown in FIG. 6. The resulting radius of gyration and hydrodynamic radius have been determined and their ratio is 0.97, which indicates that a vesicular structure has been formed. Furthermore, the average molecular weight of the particle is 4478 kDa, which tells, on average, each particle composed of approximately 7000 SHMP, 1500 iron and 120 chitosan molecules.

TEM studies have also been performed to have a direct view on the morphology of these particles. It appears (pictures not shown) that the particles are spherical with a hollow core. This is in line with the indication of SLS studies that these particles are vesicular structures. TEM samples were dried on copper grid, and iron ions were condensed and associated around the particles during drying, however the iron concentration inside the particle can not change upon drying (they are protected by the vesicle bilayer). As a result, we see the "core" of these particles has less density comparing with the surrounding.

The invention claimed is:

1. A process for the manufacture of a metal containing complex coacervate core micelle having average particle size as measured by dynamic light scattering of between 10 and 150 nm and comprised of 80 to 99 wt. % of a negatively charged chelating agent, 0.2 to 10 wt.-% of a low molecular weight natural food-grade polymeric cation, and 0.5 to 10 wt.-% of a metal cation, and water, wherein wt. % is a dry weight percent based on total weight of the complex coacervate core micelle, wherein the process comprises the steps of:
   i) preparing an aqueous solution (A) comprising a concentration of between 1 and 500 mM of the negatively charged chelating agent;
   ii) preparing an aqueous solution (B) comprising a concentration of between 1 and 500 mM of the metal salt;
   iii) forming a chelated metal solution (C) by mixing at equimolar concentration 100 parts of the aqueous solution (A) comprising the negatively charged chelating agent with 20 parts of the aqueous solution (B) comprising the metal salt to form the chelated metal solution (C), and thereafter incubating the resulting chelated metal solution (C) at room temperature for 5 minutes to 5 days,
   iv) preparing an aqueous solution (D) of a low molecular weight natural food-grade polymeric cation at a concentration of between 0.1 to 1 mg/ml in a citric acid buffer solution at pH between 4 and 6, and
   v) adding drop-wise the chelated metal solution (C) to 880 parts of the aqueous solution (D) while stirring.

2. A process for the manufacture of a metal containing complex coacervate core micelle having average particle size as measured by dynamic light scattering of between 10 and 150 nm and comprised of 80 to 99 wt. % of a negatively charged chelating agent, 0.2 to 10 wt.-% of a low molecular weight natural food-grade polymeric cation, and 0.5 to 10 wt.-% of a metal cation, and water, wherein wt. % is a dry weight percent based on total weight of the complex coacervate core micelle, wherein the process comprises the steps of:
   i) preparing an aqueous solution (A) of the negatively charged chelating agent;
   ii) preparing an aqueous solution (B) of the metal salt;
   iii) forming a chelated metal solution (C) by mixing at equimolar concentration 100 parts of the aqueous solution (A) comprising the negatively charged chelating agent with 20 parts of the aqueous solution (B) comprising the metal salt to form the chelated metal solution (C), and thereafter incubating the resulting chelated metal solution (C) at room temperature;
   iv) preparing an aqueous solution (D) of a low molecular weight natural food-grade polymeric cation in a citric acid buffer solution at pH between 4 and 6; and
   v) adding drop-wise the chelated metal solution (C) to 880 parts of the aqueous solution (D) while stirring, wherein
   the metal salt is $FeSO_4$, and the low molecular weight natural food grade polymeric cation is chitosan with a polymerisation degree between 10 and 20.

3. The process according to claim 2, wherein the negatively charged chelating agent is sodium hexametaphosphate, and wherein the sodium hexametaphosphate and $FeSO_4$ in the aqueous solutions (A) and (B) of steps i) and ii), respectively, are each at a concentration of 100 mM, and wherein the chitosan in the aqueous solution (D) of step iv) is at a concentration of 0.6 mg/ml.

4. The process according to claim 2, wherein
   the metal chelating agent in the aqueous solution (A) is at a concentration between 1 and 500 mM,
   the metal salt in the aqueous solution (B) is at a concentration between 1 and 500 mM,
   the incubation of the chelated metal solution (C) according to step iii) is performed for 5 minutes to 5 days, and
   the low molecular weight natural food-grade polymeric cation in the aqueous solution (D) is at a concentration between 0.1 to 1 mg/ml.

* * * * *